US012048581B2

(12) United States Patent
Bremer

(10) Patent No.: US 12,048,581 B2
(45) Date of Patent: Jul. 30, 2024

(54) ACTIVE STETHOSCOPE

(71) Applicant: Welch Allyn, Inc., Skaneateles Falls, NY (US)

(72) Inventor: Edward Bremer, Penfield, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 455 days.

(21) Appl. No.: 17/331,930

(22) Filed: May 27, 2021

(65) Prior Publication Data

US 2021/0369234 A1 Dec. 2, 2021

Related U.S. Application Data

(60) Provisional application No. 63/032,037, filed on May 29, 2020.

(51) Int. Cl.

*A61B 7/04* (2006.01)
*A61B 5/024* (2006.01)
*A61B 5/1455* (2006.01)
*A61B 5/28* (2021.01)

(52) U.S. Cl.

CPC ............ *A61B 7/04* (2013.01); *A61B 5/02416* (2013.01); *A61B 5/1455* (2013.01); *A61B 5/28* (2021.01); *A61B 2560/04* (2013.01)

(58) Field of Classification Search

CPC ..... A61B 7/04; A61B 5/02416; A61B 5/1455; A61B 5/28; A61B 2560/04

See application file for complete search history.

(56) References Cited

U.S. PATENT DOCUMENTS 6,438,238 B1 * 8/2002 Callahan .............. A61B 5/6843 D24/134
8,301,232 B2 10/2012 Albert et al.
8,509,882 B2 8/2013 Albert et al.
8,838,218 B2 9/2014 Khair (Continued)

FOREIGN PATENT DOCUMENTS

CN 105726017 A 7/2016
CN 206295352 U 7/2017

(Continued)

OTHER PUBLICATIONS

KardiaMobile EKG Monitor—Instant EKG on Your Phone by AliveCor—AliveCor Inc .; https://store.alivecor.com/products/kardiamobile; accessed on May 27, 2021.

*Primary Examiner* — Tammie K Marlen
*Assistant Examiner* — Maria Catherine Anthony
(74) *Attorney, Agent, or Firm* — Price Heneveld LLP

(57) ABSTRACT

A stethoscope includes a housing that has a first surface and a second surface. The first surface defines a first groove on a first side of the housing and a second groove on a second side of the housing. A photoplethysmogram sensor assembly is operably coupled to the housing and is configured to obtain and push data to a controller. The photoplethysmogram sensor assembly includes a first optical sensor disposed in the first groove and a second optical sensor disposed in the second groove. Each of the first optical sensor and the second optical sensor includes an emitter and a detector. A phonocardiogram sensor is coupled to the second surface of the housing and is configured to obtain and push data to the controller.

20 Claims, 5 Drawing Sheets

(56) References Cited

U.S. PATENT DOCUMENTS

| | | | | |
|---|---|---|---|---|
| 2005/0078533 | A1 | 4/2005 | Vyshedskiy et al. | |
| 2007/0276632 | A1* | 11/2007 | Banet | A61B 5/0245 340/573.2 |
| 2008/0013747 | A1* | 1/2008 | Tran | A61B 5/0295 381/67 |
| 2009/0316925 | A1 | 12/2009 | Eisenfeld et al. | |
| 2010/0210959 | A1 | 8/2010 | Karo | |
| 2015/0327775 | A1 | 11/2015 | Carter | |
| 2015/0359471 | A1 | 12/2015 | Sperry | |
| 2016/0296200 | A1 | 10/2016 | Hinojosa | |
| 2017/0185737 | A1 | 6/2017 | Kovacs | |
| 2018/0256061 | A1 | 9/2018 | Landgraf et al. | |
| 2019/0125270 | A1* | 5/2019 | Deriso | A61B 8/488 |
| 2019/0150739 | A1* | 5/2019 | Wawro | A61B 5/259 |
| 2019/0298183 | A1 | 10/2019 | Burg | |

FOREIGN PATENT DOCUMENTS

| | | | | |
|---|---|---|---|---|
| JP | 2007508861 | A | 4/2007 | |
| WO | WO-02091905 | A2 * | 11/2002 | A61B 7/04 |
| WO | 2019108044 | A1 | 6/2019 | |

* cited by examiner

ACTIVE STETHOSCOPE

CROSS-REFERENCE TO RELATED APPLICATION

This application claims priority to and the benefit under 35 U.S.C. § 119(e) of U.S. Provisional Application No. 63/032,037, filed on May 29, 2020, entitled "ACTIVE STETHOSCOPE," the disclosure of which is hereby incorporated herein by reference in its entirety.

FIELD OF THE DISCLOSURE

The present disclosure generally relates to an active stethoscope, and more particularly to an active stethoscope for home use.

SUMMARY OF THE DISCLOSURE

According to one aspect of the present disclosure, a health monitoring system includes a stethoscope configured to obtain data. The stethoscope includes a housing, a photoplethysmogram sensor assembly coupled to the housing, an electrocardiogram sensor assembly coupled to the housing, and a phonocardiogram sensor coupled to the housing. A controller is in communication with each of the photoplethysmogram sensor assembly, the electrocardiogram sensor assembly, and the phonocardiogram sensor of the stethoscope. The controller is configured to receive the data from the stethoscope and generate an alert notification in response to the data.

According to another aspect of the present disclosure, a stethoscope includes a housing that has a first surface and a second surface. The first surface defines a first groove on a first side of the housing and a second groove on a second side of the housing. A photoplethysmogram sensor assembly is operably coupled to the housing and configured to obtain and push photoplethysmogram data to a controller. The photoplethysmogram sensor assembly includes a first optical sensor operably coupled to the housing within the first groove and a second optical sensor operably coupled to the housing within the second groove. A phonocardiogram sensor is coupled to the second surface of the housing and configured to obtain and push phonocardiogram data to the controller.

According to another aspect of the present disclosure, a medical device includes a housing having a first surface and a second surface. The second surface has a recessed region that defines a recess. A phonocardiogram sensor is coupled to the housing within the recess. The phonocardiogram sensor is configured to obtain phonocardiogram data. An electrocardiogram sensor assembly is coupled to the housing. The electrocardiogram sensor assembly includes a first electrode and a second electrode to obtain electrocardiogram data. A controller is in communication with the phonocardiogram sensor and the electrocardiogram sensor assembly and configured to process the phonocardiogram data and the electrocardiogram data.

These and other features, advantages, and objects of the present disclosure will be further understood and appreciated by those skilled in the art by reference to the following specification, claims, and appended drawings.

DETAILED DESCRIPTION

Figure 1:
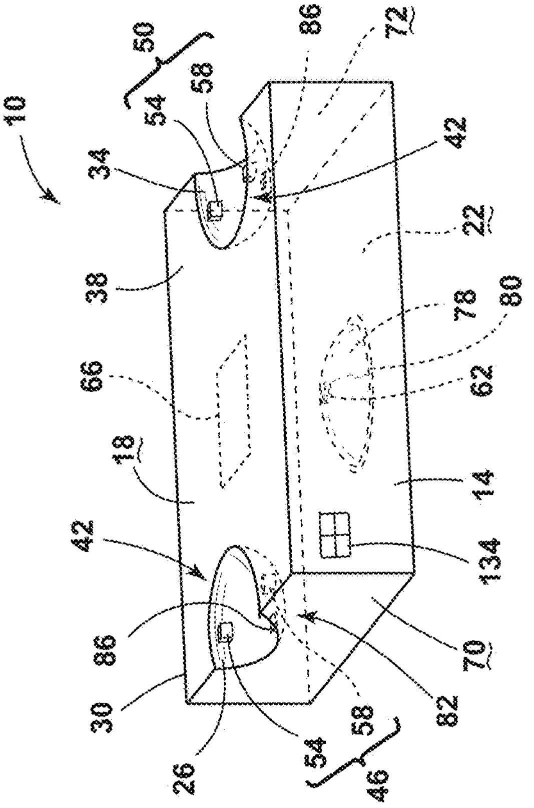
FIG. 1 is a side perspective view of a stethoscope, according to the present disclosure.

The present illustrated embodiments reside primarily in combinations of method steps and apparatus components related to an active stethoscope. Accordingly, the apparatus components and method steps have been represented, where appropriate, by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, like numerals in the description and drawings represent like elements.

For purposes of description herein, the terms "upper," "lower," "right," "left," "rear," "front," "vertical," "horizontal," and derivatives thereof, shall relate to the disclosure as oriented in FIG. 1. Unless stated otherwise, the term "front" shall refer to a surface closest to an intended viewer, and the term "rear" shall refer to a surface furthest from the intended viewer. However, it is to be understood that the disclosure may assume various alternative orientations, except where expressly specified to the contrary. It is also to be understood that the specific structures and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The terms "including," "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises a . . . " does not, without more constraints, preclude the existence of additional identical elements in the process, method, article, or apparatus that comprises the element.

Referring to FIGS. 1-10 reference numeral 10 generally designates a medical device, such as a stethoscope that includes a housing 14 that has a first surface 18 and a second surface 22. The first surface 18 defines a first groove 26 on a first side 30 of the housing and a second groove 34 on a second side 38 of the housing 14. A photoplethysmogram (PPG) sensor assembly 42 is configured to obtain and push or communicate data. The PPG sensor assembly 42 includes a first optical sensor 46 disposed in the first groove 26 and a second optical sensor 50 disposed in the second groove 34. Each of the first optical sensor 46 and the second optical sensor 50 includes an emitter 54 and a detector 58. A phonocardiogram (PCG) sensor 62 is coupled to the second surface 22 of the housing 14 and is configured to obtain and push or transmit data. A controller 66 is configured to receive the data from each of the PPG sensor assembly 42 and the PCG sensor 62.

Referring to FIG. 1, the stethoscope 10 is generally a handheld device. The stethoscope 10 includes a housing 14, which may be elongated and flat. The generally small, elongated, and flat housing 14 may allow a user to conveniently move the stethoscope 10 to certain positions to obtain physiological data. Additionally, the size and portability of the stethoscope 10 may be advantageous for providing convenient at-home health monitoring for the user.

The first surface 18, which may be a top surface, of the housing 14 defines the first groove 26 and the second groove 34. The first groove 26 can be at least partially defined by the first surface 18 and by a side surface 70. Similarly, the second groove 34 can be at least partially defined by the first surface 18 and partially defined by an opposing side surface 72. In examples where the housing 14 is elongated, the first groove 26 and the second groove 34 are generally positioned along a longitudinal extent 74 and on opposing sides of the housing 14.

Each of the first groove 26 and the second groove 34 are generally contoured to fit a finger (any finger, including a thumb) of the user. Accordingly, the user can hold the stethoscope 10 in both hands with a single finger from one hand disposed in the first groove 26 and a single finger from the other hand disposed in the second groove 34. When grasping the stethoscope 10 to have a finger positioned in each of the first groove 26 and the second groove 34, the stethoscope 10 may obtain physiological data as described further herein.

Figure 2:
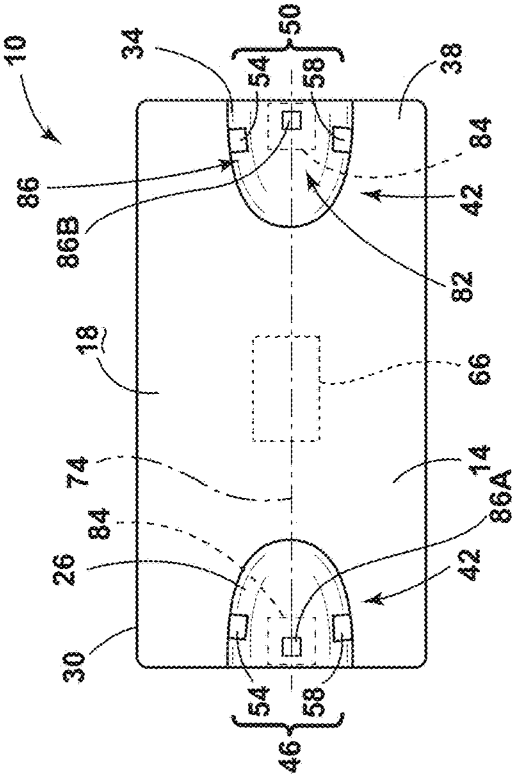
FIG. 2 is a top plan view of a stethoscope having grooves with a photoplethysmogram sensor and an electrode, according to the present disclosure.
Figure 3:
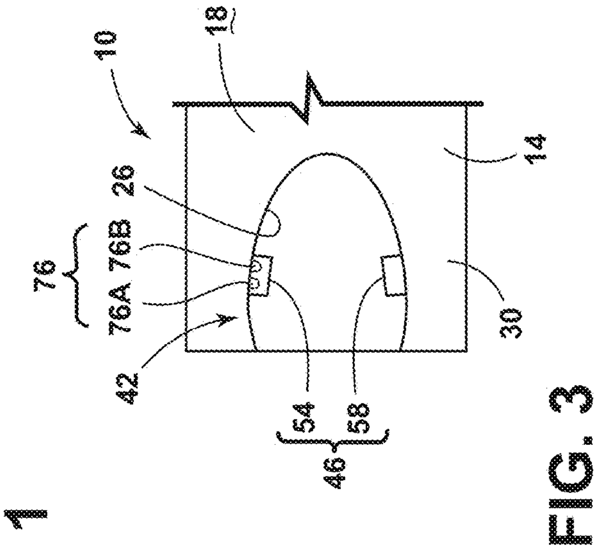
FIG. 3 is a partial top plan view of the groove of FIG. 2 with the photoplethysmogram sensor.

Referring to FIGS. 2 and 3, the stethoscope 10 includes the PPG sensor assembly 42. The PPG sensor assembly 42 is configured to obtain PPG data (e.g., the physiological data) using the first optical sensor 46 and the second optical sensor 50. The first optical sensor 46 is coupled to the housing 14 within the first groove 26. The second optical sensor 50 is coupled to the housing 14 in the second groove 34. When the stethoscope 10 is held by the user, the first optical sensor 46 engages the finger of one hand of the user, and the second optical sensor 50 engages the finger of the other hand of the user.

Each of the first optical sensor 46 and the second optical sensor 50 includes the emitter 54 and the detector 58. In a non-limiting example, the emitter 54 includes a light-emitting diode (LED) 76, and the detector 58 is configured as a photodiode. The emitter 54 may include one or more LED light sources 76. For example, the emitter 54 may include a first LED light source 76A configured to emit visible light (e.g., having a wavelength in a range between about 380 nm and about 700 nm), which can be white light (e.g., having a wavelength in a range between about 400 nm and about 700 nm) or red light (e.g., having a wavelength in a range between about 620 nm and about 750 nm) and a second LED light source 76B configured to emit infrared light (e.g., having a wavelength in a range between about 700 nm and about 1050 nm). The two light sources 76A, 76B may be advantageous as red light may be primarily absorbed by deoxygenated blood and infrared light may be primarily absorbed by oxygenated blood. The first and second light sources 76A, 76B are collectively referred to herein as the light sources 76.

The light sources 76 may include any form of light source. For example, fluorescent lighting, light-emitting diodes (LEDs), organic LEDs (OLEDs), polymer LEDs (PLEDs), laser diodes, quantum dot LEDs (QD-LEDs), solid-state lighting, a hybrid, and/or any other similar device. Any other form of lighting may be utilized within the stethoscope 10 without departing from the teachings herein. Further, various types of LEDs are suitable for use within the stethoscope 10, including, but not limited to, top-emitting LEDs, side-emitting LEDs, and others.

According to various aspects, the light sources 76 of the emitter 54 are generally configured to generate pulse profile signals based on the light received by the detector 58 and, consequently, the amount of light absorbed or reflected by the blood. The pulse profile signals may be used to calculate additional physiological data, such as blood oxygen saturation or $SpO_2$ levels, including, for example, capillary oxygen saturation levels. The $SpO_2$ level is generally an indication of a profusion of oxygen into the blood. Additionally or alternatively, the data from the PPG sensor assembly 42 may be utilized to determine blood volume changes in a microvascular bed of tissue.

The light emitted by the emitter 54 is configured to pulse through the finger of the user and be received by the detector 58. The light received by the detector 58 can be converted into an electrical pulse by the detector 58. The detector 58 is configured to send the PPG data (e.g., the electrical pulse) to the controller 66. Further, an amount of light reflected or absorbed by the blood may be determined. The amount of infrared light versus the amount of red light received by the detector 58 may indicate an absorption ratio. The controller 66 is configured to utilize the PPG data, including the peaks and averages of the pulse profile signals and/or the absorption ratio, to calculate the $SpO_2$ levels of the user. Accordingly, the controller 66 utilizes the PPG data to determine the percentage of oxygen in the blood (e.g., 99%, 89%, etc.).

The data received from the PPG sensor assembly 42 by the controller 66 may be utilized to measure or determine pulse transit time (PTT) and pulse velocity time (PVT) or pulse wave velocity (PWV) between different locations of the body of the user. The PTT and/or the PVT may be calculated based on the timing in the pulse profile signals and/or the $SpO_2$ measurements. The controller 66 may measure the time delay between critical points of the PPG data signal. The critical points are characteristic identification points of the blood pulse wave. The PTT and/or the PVT may be indicative of the time it takes the pulse pressure waveform to propagate through a length of the arterial tree. Generally, PTT is the propagation time of a pulse wave going from the heart to the peripheral arteries and may be calculated as time between R-peaks of an electrocardiogram (ECG) to the time to the pulse wave peaks of a photoplethysmogram (PPG). Alternatively, the PTT may be calculated as the time from the pulse wave peaks of the PPG on a finger of one hand to the pulse wave peaks of the PPG on a finger of the other hand. The PVT may be calculated as the time the pulse wave from the heart to the selected artery divided by the distance and multiplied by a constant (e.g., 0.8).

The PVT and/or the PTT may be utilized to calculate the blood pressure of the user. Generally, PTT is inversely proportional to blood pressure. Additionally, PVT is generally inversely related to PTT. PVT may be utilized to determine arterial stiffness, which may indicate cardiovascular disease. The PTT and PVT measurements may be utilized to monitor cardiovascular concerns or disease in the user.

Figure 4:
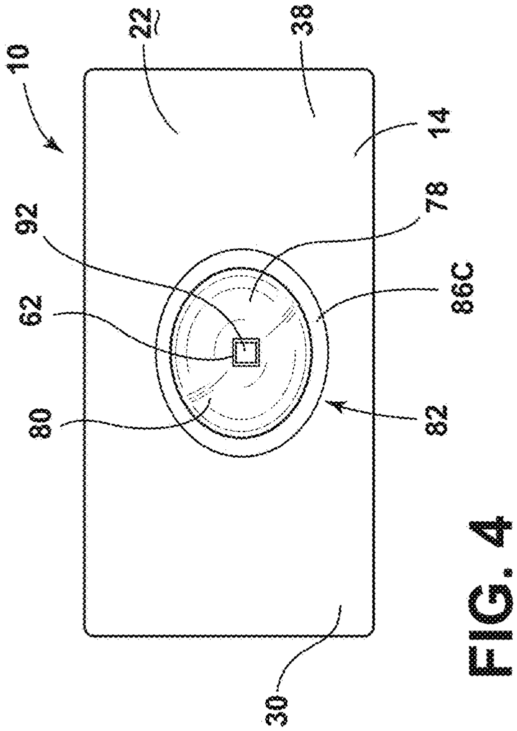
FIG. 4 is a bottom plan view of a stethoscope having a recess with a phonocardiogram sensor, according to the present disclosure.
Figure 5:
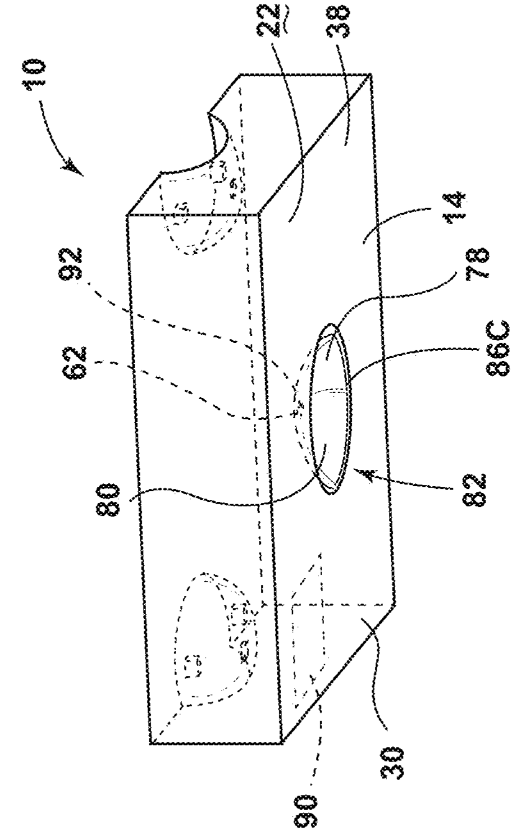
FIG. 5 is a bottom perspective view of a stethoscope having a recess defined in a second surface thereof, according to the present disclosure.

Referring to FIGS. 2, 4, and 5, the stethoscope 10 has a recessed region 78 on the second surface 22 that defines a space or recess 80. An ECG sensor assembly 82 is at least partially coupled to the second surface 22 adjacent to the recess 80. The ECG sensor assembly 82 is utilized to measure ECG data (e.g., physiological data), such as the six (6) lead ECG values. Additionally, the ECG sensor assembly 82 may be coupled with a capacitor-sensing circuit 84 for activating the stethoscope 10 to obtain the physiological data, as described further herein.

The ECG sensor assembly 82 may include a first electrode 86A is disposed within the first groove 26, a second electrode 86B is disposed within the second groove 34, and a third electrode 86C is disposed in an annular ring surrounding the recess 80. The first, second, and third electrodes 86A-86C are collectively referred to herein as electrodes 86 or metal electrodes 86. The ECG sensor assembly 82 is coupled to the first surface 18 and the second surface 22 of the housing 14 for convenient use for the user.

Figure 6:
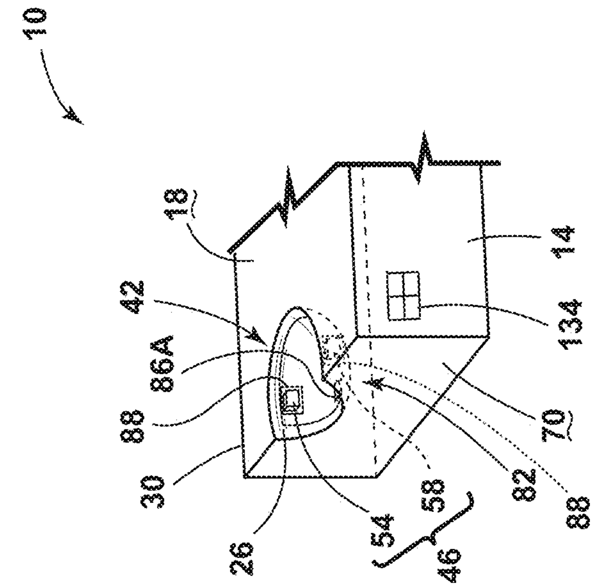
FIG. 6 is a partial side perspective view of a stethoscope having a photoplethysmogram sensor and an electrode for an electrocardiogram sensor within a groove, according to the present disclosure.

The electrodes 86A, 86B disposed in each of the first groove 26 and the second groove 34 may be flat contact surfaces. Alternatively, the electrodes 86A, 86B in the first and second grooves 26, 34 may be contoured to the shape of the first and second grooves 26, 34. As illustrated in FIG. 2, the electrodes 86A, 86B can cover a portion of the surfaces of the first groove 26 and the second groove 34. It is also contemplated that the electrodes 86A, 86B may be contoured to cover a substantial portion, or all, of the surface of each of the first groove 26 and the second groove 34 (as best illustrated in FIG. 6).

The ECG sensor assembly 82 may provide a passive differential voltage measuring system to the stethoscope 10. The ECG sensor assembly 82 is configured to obtain the ECG data and send the ECG data to the controller 66. The ECG data may include the six (6) lead ECG measurements, which include Lead I, Lead II, Lead III, aVR, aVL, and aVF measurements. The Lead I, Lead II, and Lead III measurements are bipolar limb leads using electrodes 86 of opposite polarity, and the aVR, aVL, and aVF measurements are unipolar limb leads. The six (6) lead ECG measurements measure approximately 360° around the heart, which allows the stethoscope 10 to generally pinpoint a location of a heart issue.

Referring still to FIGS. 2 and 4, the third electrode 86C of the ECG sensor assembly 82 is disposed proximate to and extends around the recess 80 on the second surface 22 of the housing 14. The third electrode 86C is generally a metal contact annular ring on the second surface 22 of the stethoscope 10. The third electrode 86C is positioned and shaped to come into contact with skin in a generally flat area of the body, such as the chest, leg, or knee. The generally flat annular ring configuration of the third electrode 86C provides for proper contact between the electrode 86C and the skin of the user. The stethoscope 10 generally has three electrodes 86 with one electrode 86A, 86B in each of the first groove 26 and the second groove 34 on the first surface 18 of the stethoscope 10 and one electrode 86C around the recess 80 on the second surface 22 of the stethoscope 10.

In use, it is generally contemplated that the user can hold the stethoscope 10 with a single finger from each hand in contact with the electrodes 86A, 86B within the first groove 26 and the second groove 34. When the user is in contact with the electrodes 86A, 86B, the stethoscope 10 can measure the voltage across the chest of the user for the Lead I ECG measurement. While maintaining contact with the electrodes 86A, 86B, the user can move the stethoscope 10 to place the third electrode 86C on the second surface 22 in contact with another part of the body. For example, when the third electrode 86C is in contact with the left knee of the user, the stethoscope 10 can measure the voltage for the Lead II and Lead III ECG measurement. When measuring the Lead II and Lead III ECG measurements, the stethoscope 10 connects a voltage circuit from the hands of the user through the left or right shoulder to the left or right knee to obtain and measure diagonal heart signals.

The ECG data is communicated to the controller 66. The controller 66 may calculate the heart rate of the user utilizing the ECG data. Additionally, controller 66 may detect cardiac abnormalities using the ECG data. The location of a potential cause of the cardiac abnormality may be determined through the six (6) lead ECG measurements.

Referring to FIGS. 3 and 6, the PPG sensor assembly 42 and the ECG sensor assembly 82 may both be included in the stethoscope 10 to provide both types of physiological data to the user. The PPG sensor assembly 42 and the ECG sensor assembly 82 may sense the physiological data concurrently, independently, or a combination thereof depending on the position of the stethoscope 10 relative to the user. The electrodes 86A, 86B of the ECG sensor assembly 82 may be separate from the emitter 54 and the detector 58 of the PPG sensor assembly 42. As best illustrated in FIG. 3, the first optical sensor 46 may extend into the space defined by the first groove 26. The finger of the user can be in contact with each of the emitter 54 and detector 58. It is also contemplated that the first optical sensor 46 may be disposed within the housing 14, such that the first optical sensor 46 may not impinge the space defined by the first groove 26. The first optical sensor 46 may be flush with or behind the surface of the first groove 26. The flush configuration of the PPG sensor assembly 42 may be advantageous for combining the PPG sensor assembly 42 with the ECG sensor assembly 82 (FIG. 2). While the first optical sensor 46 in the first groove 26 is illustrated, it is contemplated that the second optical sensor 50 in the second groove 34 (FIG. 2) may have a substantially similar configuration.

As best illustrated in FIG. 6, the electrodes 86A, 86B may be contoured to correspond with the shape of each of the first groove 26 and the second groove 34 and extend over an increased surface area within the first and second grooves 26, 34. In such configurations, the electrodes 86A, 86B and/or the housing 14 may define optically clear windows 88 that align with the emitter 54 and the detector 58 of each of the first optical sensor 46 and the second optical sensor 50. The optically clear windows 88 allow the light to be emitted through the windows 88 by the emitter 54 and received through the windows 88 by the detector 58.

Additionally or alternatively, the electrodes 86A, 86B may not define the windows 88. In such examples, the housing 14 defines the optically clear windows 88. The emitter 54 and the detector 58 are aligned with the windows 88 defined by the housing 14. The emitter 54 and the detector 58 may be positioned within the housing 14 and emit or detect light, respectively, through the windows 88.

Referring again to FIGS. 2, 4, and 5, the electrodes 86 of the ECG sensor assembly 82 may be utilized to measure an impedance signal through the body of the user. Impedance is generally a measure of restriction applied to the electrical circuit of the heart. The impedance signal may be utilized to measure body mass index, body fat levels, and fluid levels within the body. When the user has a finger in contact with each of the electrodes 86A, 86B within the first groove 26 and the second groove 34, the stethoscope 10 may measure the impedance across the chest of the user.

In certain aspects, one of the electrodes 86A may apply a small electric current to be detected by the other electrode 86B. A power supply 90 of the stethoscope 10 may provide the current for impedance measurement. The voltage received by the second electrode 86B varies based on the biological material through which the current passes (e.g., bone, muscle, fat, etc.). The variance in the voltage received may be utilized by the controller 66 to determine the impedance signal.

In various aspects, the user can touch the third electrode 86C disposed around the recess 80 to the right knee or the left knee. When the third electrode 86C contacts the knee while the fingers remain in contact with the electrodes 86A, 86B within the first groove 26 and the second groove 34, the stethoscope 10 can measure a portion of the impedance of the arms of the user and down to the leg. The measurements may be utilized to measure the sub-impedance for each arm and each leg of the user.

The sub-impedance measurements may indicate the fluid level within each arm and each leg for the particular measurements taken through the body. The body can act as a resistor to calculate the impedance signal. The various vectors between the chest, the left leg, and the right leg can be utilized to calculate sub-impedance measurements for a leg portion, an entire leg, an arm proportion, or an entire arm of the user. The impedance circuit (e.g., using the electrodes 86) can drive a current into the fingers of the user and into the body that can be utilized to measure the body fat content and the body water content. Measuring the fluid levels within the body may be advantageous for various patients, including patients with lymphedema. The user of the stethoscope 10 can measure impedance daily, weekly, or at regular or irregular intervals, and compare the obtained data to a baseline to determine variations in the body mass index, the body fat level, and the body fluid level.

Referring still to FIGS. 4 and 5, the PCG sensor 62 may be coupled to the second surface 22 of the housing 14. The second surface 22 of the housing 14 defines the recess 80, and the PCG sensor 62 generally includes a microphone 92 positioned at a bottom of the recessed region 78. The microphone 92 is generally centrally located within the recess 80. The recess 80 is contoured to direct sound to the microphone 92 or other acoustic sensors. In various examples, the recess 80 may be bell-shaped, parabolic, arcuate, hemispherical, partially ovoid, etc. to direct sounds to the microphone 92.

The recess 80 is generally centrally located on the second surface 22. It is contemplated that the recess 80 may be located in any practicable location and/or be any shape, such that the recess 80 can engage various parts of the body of the user. For example, the recessed region 78 can be contoured to engage a chest, a knee, and/or an ankle of the user. It is contemplated that an edge between the recessed region 78 and the remainder of the second surface 22 may be rounded or beveled to assist in better aligning the recess 80 with more bony prominences.

The recess 80 may be defined on an opposing surface relative to the first groove 26 and the second groove 34. In various examples, though on the opposing surface, the recess 80 is positioned between and generally equidistant from each of the first groove 26 and the second groove 34. This configuration may be advantageous for convenient handling by the user to obtain one of both or the PPG data and the ECG data concurrently with the PCG data.

The PCG sensor 62 is generally utilized to measure the heart sounds of the user. The user can place the stethoscope 10 against the chest with the second surface 22 of the housing 14 in contact with the chest. The recessed region 78 and the recess 80 direct the sounds of the heart to the microphone 92. The PCG sensor 62 can measure the S1 and S2 heart sounds. Generally, the S1 and S2 heart sounds mark valve closings. The S1 heart sound represents the closure of the atrioventricular valves and corresponds with the pulse of the user. The S2 heart sound represents the closure of the semilunar valves. The PCG data is communicated to the controller 66 (FIG. 1). The measured heart sounds may be utilized to calculate at least one of PTT, PVT, and $SpO_2$ levels.

Additionally, the S1 and S2 sounds may be utilized to monitor cardiac conditions of the user. For example, abnormal S2 sounds may be indicative of various cardiac conditions, such as, for example, pulmonary hypertension. It is also contemplated that the PCG sensor 62 may also sense S3 heart sounds and S4 heart sounds. When sensed, the S3 and S4 heart sounds may be associated with ventricular dilation (e.g., ventricular systolic failure) or a stiff and low compliance ventricle (e.g., ventricular hypertrophy), respectively. Moreover, any additional sounds, such as heart murmurs, may be sensed and monitored using the stethoscope 10.

Referring again to FIGS. 1-6, the sensed data may be utilized to determine various physiological data or vital sign parameters of the user. For example, the PTT is the interval between the peak of the R-wave in an ECG measurement and the fingertip PPG measurement. The S1 and S2 heart sounds measured by the PCG sensor 62 may contribute to the calculation of PTT. The controller 66 may measure the time delay between the R-peak and any one critical point of the PPG signal to calculate the PTT.

The PCG data and the PPG data, along with the PVT and the PTT, may be utilized to measure the blood pressure of the user. PTT may be used to estimate systolic blood pressure and diastolic blood pressure. PVT, related to arterial stiffness, may be modulated by blood pressure. The data obtained by the stethoscope 10 may be utilized to calibrate a blood pressure measurement and obtain blood pressure deltas. The stethoscope 10 may then calculate blood pressure over a predetermined amount of time using the calibration. The predetermined amount of time (i.e., hours, days, etc.) may differ depending on signal quality and various other factors.

Figure 7:
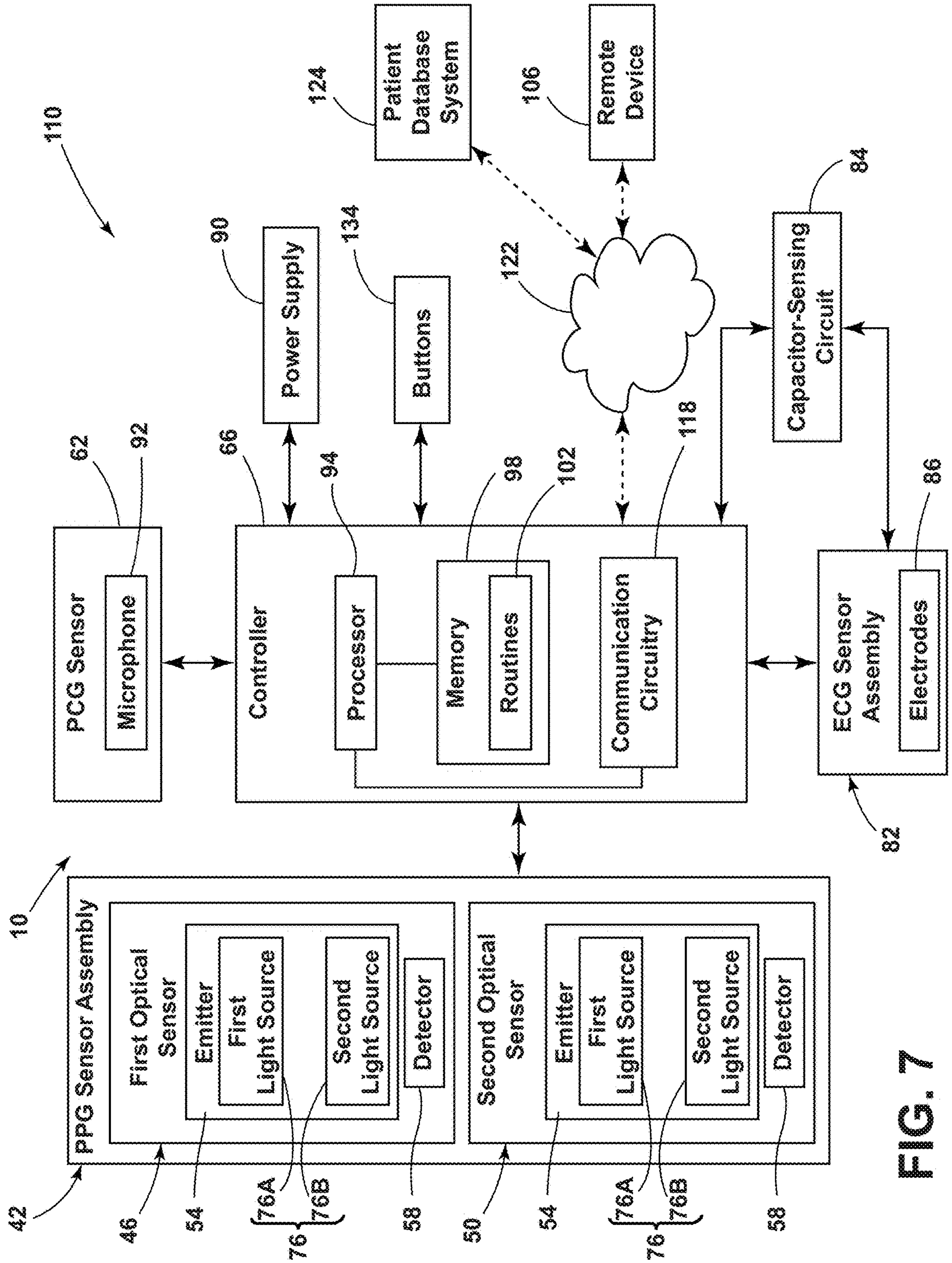
FIG. 7 is a block diagram of a health monitoring system including a stethoscope, according to the present disclosure.

Referring to FIG. 7, the stethoscope 10 includes the controller 66. The controller 66 includes a processor 94, a memory 98, and other control circuitry. Instructions or routines 102 are stored within the memory 98 and executable by the processor 94. The controller 66 disclosed herein may include various types of control circuitry, digital or analog, and may include the processor 94, a microcontroller, an application specific circuit (ASIC), or other circuitry configured to perform the various input or output, control, analysis, or other functions described herein. The memory 98 described herein may be implemented in a variety of volatile and nonvolatile memory formats. The routines 102 include operating instructions to enable various methods and functions described herein.

The controller 66 generally includes at least one routine 102 related to receiving the physiological data from each of the PPG sensor assembly 42, the PCG sensor 62, and the ECG sensor assembly 82. The routines 102 may also include instructions for utilizing the data received to calculate additional vital sign parameters or physiological data, including, but not limited to, blood oxygen saturation levels ($SpO_2$), PVT, PTT, heart rate, blood pressure, impedance, body composition, and fluid levels in the body.

The controller 66 is configured to receive the physiological data from each of the PPG sensor assembly 42, the PCG sensor 62, and the ECG sensor assembly 82 and communicate the physiological data through a data line or wirelessly to a remote device 106. The remote device 106 may utilize the data to determine additional data or parameters, store the data, and/or compare the data over a period of time. The stethoscope 10 and the remote device 106 may be included in a health monitoring system 110 that measures and tracks vital sign parameters or physiological data of the user. The stethoscope 10 is configured to obtain physiological data, which is conveyed to the remote device 106 by the controller 66. The physiological data includes each type of data received by the controller 66 (e.g., the PPG data, the PCG data, the ECG data, the impedance data, etc.) and the physiological data calculated therefrom.

The controller 66 includes communication circuitry 118 configured to communicate with the remote device 106 and/or remote servers (e.g., cloud servers, Internet-connected databases, computers, etc.) via a communication interface 122. The communication interface 122 may be a network having one or more various wired or wireless communication mechanisms, including any combination of wired (e.g., cable and fiber) or wireless communications and any network topology or topologies. Exemplary communication networks include wireless communication networks, such as, for example, a Bluetooth® transceiver, a ZigBee® transceiver, a Wi-Fi transceiver, an IrDA transceiver, an RFID transceiver, etc. The controller 66 of the stethoscope 10 and the remote device 106 may include circuitry configured for bidirectional wireless communication. Additional exemplary communication networks include local area networks (LAN) and/or wide area networks (WAN), including the Internet and other data communication services. It is contemplated that the stethoscope 10 and the remote device 106 may communicate by any suitable technology for exchanging data.

The remote device 106 may be a remote handheld unit such as, for example, a phone, a tablet, a portable computer, a wearable device, etc. In a non-limiting example, the remote device 106 can be associated with a medical professional through a patient database system 124. The remote device 106 may include an application or software for communicating information between the medical professional and the user. The physiological or vital sign data may be communicated from the stethoscope 10 through the communication interface 122 to the patient database system 124. The remote device 106 may also be in communication with the patient database system 124 to transfer data therebetween.

Figure 9:
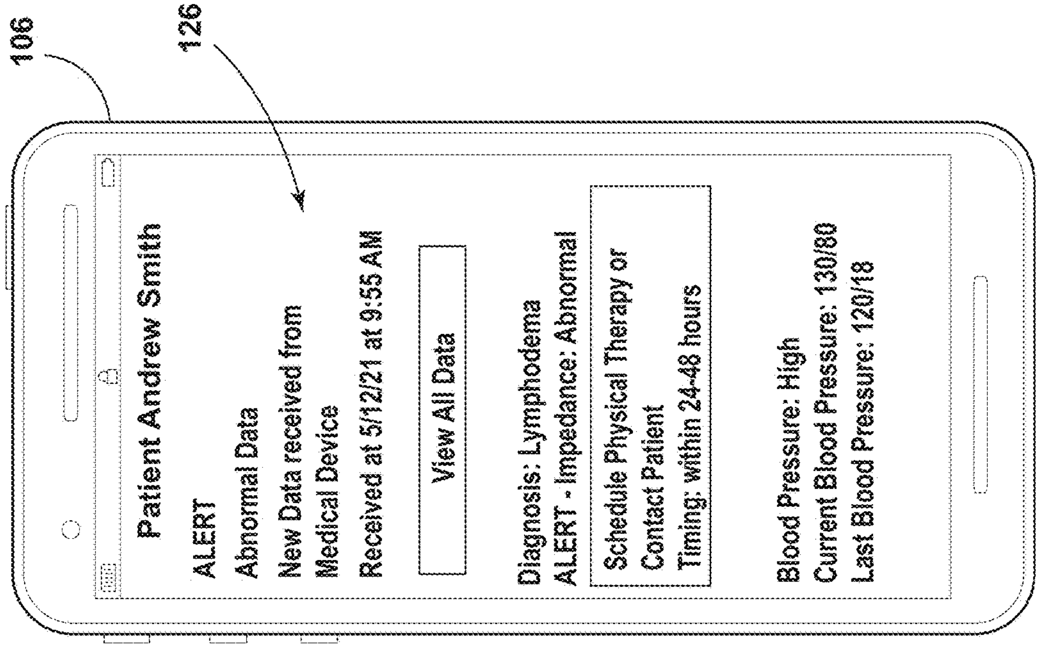
FIG. 9 is representative of an interface of a remote device for a caregiver of a user using a stethoscope, according to the present disclosure.
Figure 8:
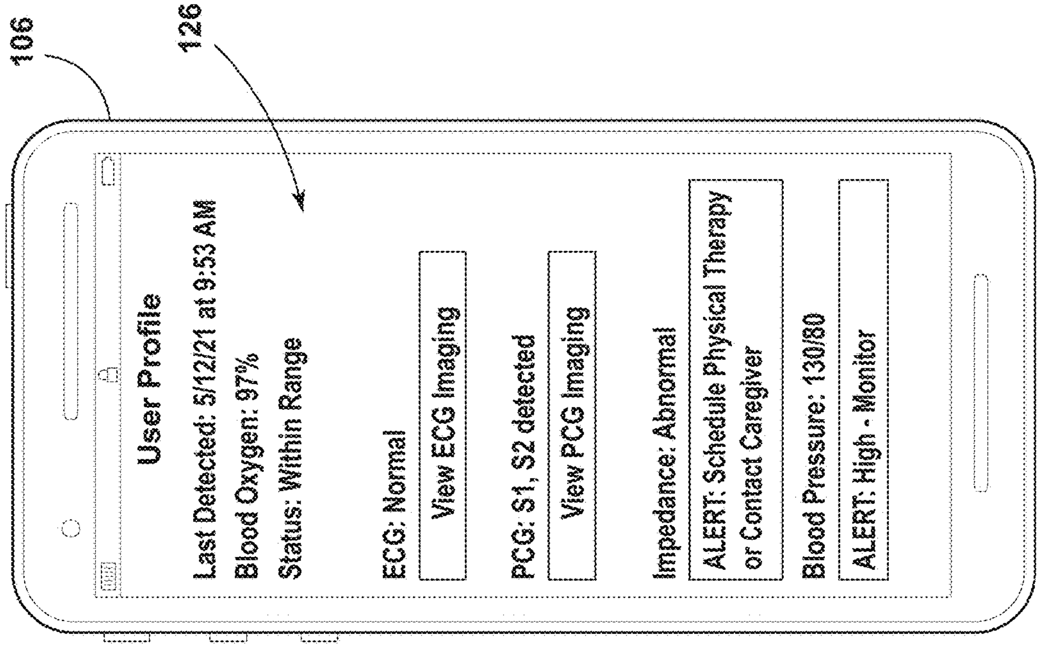
FIG. 8 is representative of an interface of a remote device for a user of a stethoscope, according to the present disclosure.

Referring still to FIG. 7, as well as FIGS. 8 and 9, the controller 66 may be configured to generate an alert notification 126 in response to the physiological or vital sign data received from the stethoscope 10. The controller 66 is configured to communicate the alert notification 126 to the remote device 106 for viewing by one of the user and the medical professional or caregiver. In certain aspects, the controller 66 of the stethoscope 10 may compare the sensed and calculated physiological data to predefined values or baseline values specific to the user. For example, if the physiological data is outside a predefined range, then the alert notification 126 may be generated. The alert notification 126 may indicate a certain condition or abnormal data to the user, as illustrated in FIG. 8, or to the medical professional or caregiver, as illustrated in FIG. 9.

As best illustrated in FIG. 8, the remote device 106 may belong to the user of the stethoscope 10, thereby allowing the user to monitor the obtained vital sign parameter data in a home environment. In such examples, the alert notification 126 may be communicated to the remote device 106, notifying the user of a certain condition or abnormal data. The user may contact the caregiver or schedule an appointment in response to the alert notification 126. As best illustrated in FIG. 9, when the alert notification 126 is generated for the medical professional, the alert notification 126 may be communicated to the patient database system 124, which may be a centralized records database accessible by the caregiver. Once communicated to the patient database system 124, the alert notification 126 may be viewed by the medical professional or caregiver associated with the user of the stethoscope 10. The medical professional may contact the user of the stethoscope 10 regarding the condition detected by the stethoscope 10 in response to the alert notification 126.

The alert notification 126 may provide the physiological data, an indication of the condition, a tip or prompt to contact the medical professional, etc. The alert notification 126 may also include selectable features to view additional data or imaging, as well as schedule appointments. The information illustrated in the alert notification 126 of FIGS. 8 and 9 is merely exemplary and not meant to be limiting. Moreover, the alert notification 126 can be any practicable alert (e.g., visual, haptic, audible, etc.) configured to convey information to the medical professional and/or the user.

Referring to FIGS. 1-9, to use the stethoscope 10, the user can grasp and hold the stethoscope 10 with one finger disposed in each of the first groove 26 and the second groove 34. For example, the thumbs of the user can be disposed in the first groove 26 and the second groove 34 and the index fingers of the user can contact the second surface 22 to hold the stethoscope 10. The emitter 54 of each of the first optical sensor 46 and the second optical sensor 50 of the PPG sensor assembly 42 emit light, which can be received by the detectors 58 to calculate or measure the pulse profile, the $SpO_2$, the absorption ration, etc. of the user. Additionally or alternatively, the thumbs or index fingers of the user can be in contact with the electrodes 86A, 86B within the first groove 26 and the second groove 34, providing electrical contact to the body to measure the voltage (e.g., the ECG signal) across the chest of the user for the Lead I ECG measurement. The user can then place the third electrode 86C disposed around the recess 80 on the kneecap to get the Lead II and the Lead III ECG measurements. The user can obtain the Lead I, the Lead II, the Lead III ECG measurements, the pulse profile, and the $SpO_2$ measurements simultaneously by holding the stethoscope 10 and placing the stethoscope 10 in contact with the kneecap.

When the user holds the stethoscope 10 and contacts the second surface 22 with the chest of the user, the user can simultaneously obtain the Lead I ECG measurement across the chest, the pulse profile, the $SpO_2$ measurements, and the heart rate using the PCG sensor 62 simultaneously. The stethoscope 10 can be used to diagram the heart ECG QRS bundles when the heart is contracting. When the heart is beating, peaks and specific points on the waveform of the ECG signal can be compared to a point of the pulse profile signal (e.g., the PPG or $SpO_2$ signal) to calculate the PTT, the PVT, and the blood pressure. Accordingly, using the PPG sensor assembly 42, the PCG sensor 62, and the ECG sensor assembly 82, the stethoscope 10 may be advantageous for obtaining a variety of physiological or vital sign data simultaneously.

The stethoscope 10 can include one or more buttons 134 on the housing 14 to activate or deactivate the stethoscope 10 or certain aspects of the stethoscope 10. The buttons 134 can correspond with measuring the PCG data, the ECG data, and/or the PPG data. Accordingly, the user can press one of the buttons 134, position the stethoscope 10, and the stethoscope 10 can take the selected measurement or measurements. The user may obtain certain measurements and not others based on the selected buttons 134 or may obtain all measurements based on the selected buttons 134. It is contemplated that the controller 66 may analyze or process the physiological data and which buttons 134 were selected. If a certain button 134 was selected but the sensed physiological data does not match the type of physiological data to be obtained, the controller 66 may generate the alert notification 126 to inform the user to obtain a subsequent measurement or contact the medical professional. For example, if the PCG sensor 62 is activated but the user does not place the stethoscope 10 against his or her chest, the PCG data may not be sensed and the controller 66 may indicate the misalignment between the activated PCG sensor 62 and the sensed data to the user.

In a specific example, the stethoscope 10 may be advantageous for lymphedema patients. Cancer patients that have their lymph nodes removed are more susceptible to lymphedema. Lymphedema is generally swelling of the arms and the legs of the patient. The measurements obtained by the stethoscope 10 can alert the medical professional and/or the user that the patient should schedule a physical therapy session to manage the lymphedema. The impedance circuit that measures the fluid level within the body may also be advantageous to monitor lymphedema patients. The stethoscope 10 may provide a long-term health monitoring system 110 for those with chronic medical concerns.

According to various aspects, the stethoscope 10 can be preprogrammed based on the specific condition and/or diagnosis of the user. The user may determine a change in health over time by using daily, weekly, or periodic measurements. The frequency of the measurements may depend on a risk level or a level of attention for the specific condition. The user and the medical professional associated with the remote device 106 can monitor any significant changes in the condition of the user of the stethoscope 10.

Referring still to FIGS. 1-9, the medical device, such as the stethoscope 10, may include any combination or each of the PPG sensor assembly 42, the PCG sensor 62, and the ECG sensor assembly 82. Based on the various configurations of the medical device, different types of physiological data may be measured.

Figure 10:
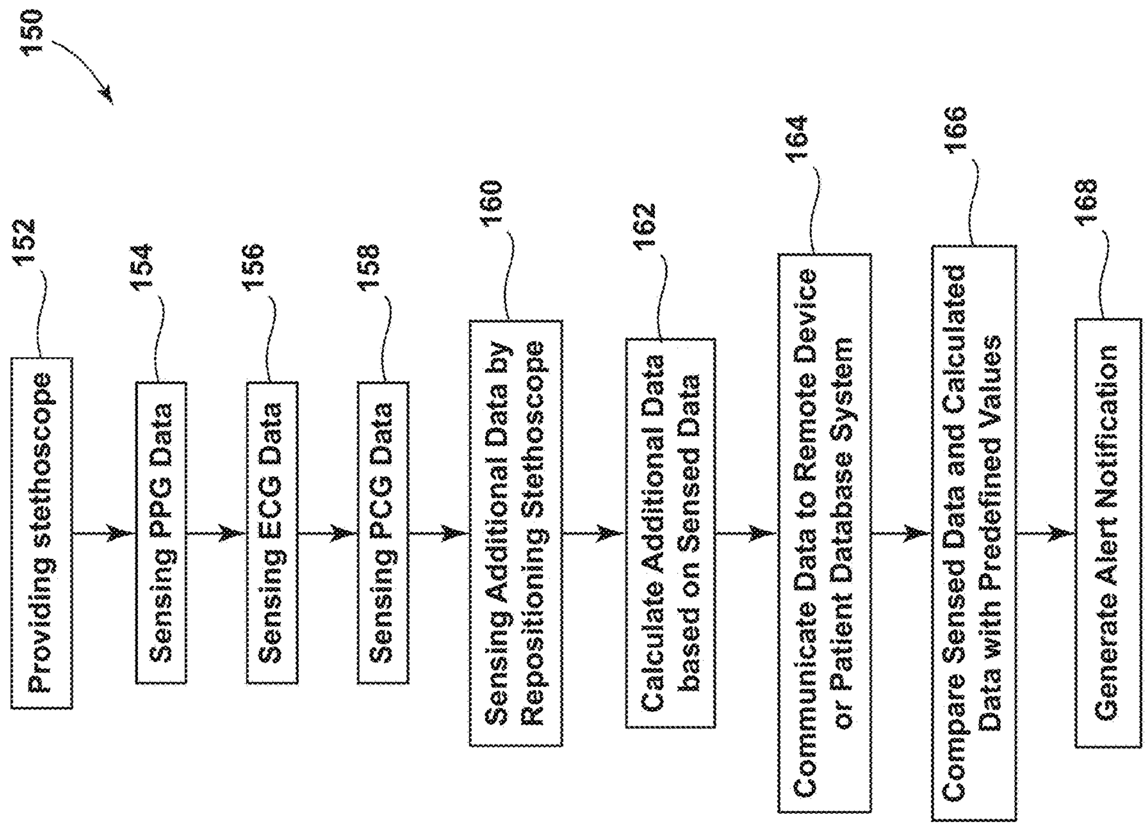
FIG. 10 is a flow diagram of a method of monitoring a health condition of a user, according to the present disclosure.

Referring to FIG. 10, as well as FIG. 1-9, a method 150 of monitoring health or medical conditions of the user includes step 152 of providing the medical device or the stethoscope 10. The stethoscope 10 may have any one or more of the PPG sensor assembly 42, the PCG sensor 62, and the ECG sensor assembly 82. In certain aspects, the sensors included in the stethoscope 10 may be customized to the user. Alternatively, the stethoscope 10 may include each of the PPG sensor assembly 42, the PCG sensor 62, and the ECG sensor assembly 82 to provide flexible at-home monitoring of various conditions.

In step 154, the PPG sensor assembly 42 may be activated to obtain the PPG data. The user may position one finger in the first groove 26 and a second finger of the other hand in the second groove 34. The user may then press one of the buttons 134 to activate the PPG sensor assembly 42.

Additionally or alternatively, the ECG electrodes 86A, 86B in the first and second grooves 26, 34 (e.g., right and left grooves) may be coupled to the capacitor-sensing circuit 84. The controller 66 may activate the PPG sensor assembly 42, the ECG sensor assembly 82, and/or the PCG sensor 62 to obtain the PPG, ECG, and PCG measurements, respectively, when the electrodes 86A, 86B are touched by the patient (e.g., touch activation). The capacitor-sensing circuit 84 may provide a voltage to one or both of the electrodes 86A, 86B to generate at least one electric field. The capacitor-sensing circuit 84 is configured to sense a change in capacitance that occurs when the user brings his or her finger into contact or close proximity with one or both of the electrodes 86A, 86B, which affects the generated electric fields. Upon the capacitor-sensing circuit 84 sensing the change in capacitance, the controller 66 is configured to activate one or more of the PPG sensor assembly 42, the PCG sensor 62, and the ECG sensor assembly 82. Accordingly, the stethoscope 10 may activate and obtain data automatically upon the user contacting the ECG sensor assembly 82. It is contemplated that the electrodes 86A, 86B and the capacitor-sensing circuit 84 may be configured to operate as any practicable type of capacitor (e.g., self-capacitance or mutual capacitance between the electrodes 86A, 86B or with additional electrodes) without departing from the teachings herein.

Upon activation, the emitter 54 transmits light toward the detector 58 through the fingers of the user. The emitter 54 may emit at least one of red light and infrared light. The light received by the detector 58 may be converted to an electrical signal and communicated to the controller 66.

In step 156, the ECG sensor assembly 82 may be activated to obtain at least some of the ECG data. The user may press at least one button 134 to activate the ECG sensor assembly 82 to begin obtaining data across the chest of the user. When the user positions his or her fingers in the first and second grooves 26, 34, the user contacts the electrodes 86A, 86B, allowing the ECG data to be measured. The ECG data may then be communicated to the controller 66.

In step 158, the PCG sensor 62 may be activated via at least one of the buttons 134 to initiate sensing of the PCG data. The user may place the second surface 22 of the stethoscope against his or her chest and activate the PCG sensor 62. Once activated, the microphone 92 is configured to sense the heart sounds of the user. The heart sounds (e.g., the PCG data) are communicated to the controller 66.

In step 160, additional data may be sensed by the stethoscope 10. For example, the user may reposition the stethoscope 10 to obtain additional ECG data. The user may position the stethoscope 10 so the electrode 86C on the second surface 22 abuts the knee or ankle of the user. Additionally or alternatively, in step 160, a voltage may be provided to the electrode 86A to measure resistance within the user to obtain impedance data. The user may also reposition the stethoscope 10 to obtain sub-impedance data for his or her arms and legs.

In step 162, the controller 66 may utilize the obtained data to calculate additional physiological or vital sign data. For example, the controller 66 may utilize the data to obtain blood oxygen saturation ($SpO_2$), PTT, PVT, blood pressure, body composition, and other related information. In step 164, the sensed data and the calculated data or information are communicated to at least one of the remote device 106 and the patient database system 124 to be viewed by the user or the medical professional. Additionally, when the information is communicated to the patient database system 124, the information may be stored within an electronic medical record associated with the user.

In step 166, the controller 66 may compare the sensed and calculated data with predefined data. The predefined data may be an upper threshold, a lower threshold, or a range. The predefined data may be defined by the medical professional and may be based on the user (age, gender, etc.). Additionally or alternatively, the predefined data may be baselines values specific to the user. In certain aspects, the baseline values may be based on certain conditions of the patient.

In step 168, the controller 66 may generate the alert notification 126. The alert notification 126 may be communicated to at least one of the medical professional and the user via the remote device 106. The alert notification 126 may include a variety of information helpful to the treatment and monitoring of the user. The alert notification 126 may include the sensed and calculated data. Additionally or alternatively, the alert notification 126 may indicate abnormal data. Further, based on the sensed or calculated data, the alert notification 126 may include steps to be taken for treatment, such as contacting the medical professional, scheduling an appointment, etc. It is understood that the steps of the method 150 may be performed in any order, simultaneously and/or omitted without departing from the teachings provided herein.

Use of the present device may provide for a variety of advantages. For example, the stethoscope 10 may include one or more of the PPG sensor assembly 42, the PCG sensor 62, and the ECG sensor assembly 82. Additionally, the stethoscope 10 can be customized based on the condition of the user of the stethoscope 10. Accordingly, the stethoscope 10 may be preprogrammed to monitor certain data based on the condition of the user. Further, after a patient is released from a hospital or other medical facility, the user can utilize the stethoscope 10 to monitor a current health status, including episodic vital sign parameters, while at home. Also, the stethoscope 10 can be utilized to monitor vital sign parameters and physiological data over longer periods of time. Accordingly, the stethoscope 10 may be utilized for overall health assessments in the home on a self-serve basis and a continuous basis. Further, the stethoscope 10 may provide a low-cost device for users to monitor vital sign and physiological data and provide indications to a medical professional and the user of any significant changes to the condition of the user. These and other benefits or advantages may be realized and/or achieved.

The device disclosed herein is further summarized in the following paragraphs and is further characterized by combinations of any and all of the various aspects described therein.

According to one aspect of the present disclosure, a health monitoring system includes a stethoscope configured to obtain data. The stethoscope includes a housing, a photoplethysmogram sensor assembly coupled to the housing, an electrocardiogram sensor assembly coupled to the housing, and a phonocardiogram sensor coupled to the housing. A controller is in communication with each of the photoplethysmogram sensor assembly, the electrocardiogram sensor assembly, and the phonocardiogram sensor of the stethoscope. The controller is configured to receive the data from the stethoscope and generate an alert notification in response to the data. According to still another aspect, a controller is configured to communicate an alert notification to a remote device to be displayed to a user.

According to another aspect, a controller is configured to determine a pulse transit time and a pulse velocity time of a user in response to data received from a photoplethysmogram sensor assembly.

According to another aspect, a controller is configured to measure an oxygen saturation level in response to data received from a photoplethysmogram sensor assembly.

According to another aspect, a housing defines a first groove and a second groove on a surface thereof. A photoplethysmogram sensor assembly and an electrocardiogram sensor assembly are at least partially disposed within the first groove and the second groove.

According to another aspect, a housing includes a recessed region on a surface thereof. A phonocardiogram sensor is coupled to the housing within the recessed region and an electrocardiogram sense assembly is at least partially coupled to the housing adjacent to the recessed region.

According to another aspect, a controller is configured to determine physiological data from at least one of photoplethysmogram data, electrocardiogram data, and phonocardiogram data. The physiological data includes at least one of blood pressure, impedance, pulse transit time, pulse velocity time, and body composition.

According to another aspect of the present disclosure, a stethoscope includes a housing that has a first surface and a second surface. The first surface defines a first groove on a first side of the housing and a second groove on a second side of the housing. A photoplethysmogram sensor assembly is operably coupled to the housing and configured to obtain and push photoplethysmogram data to a controller. The photoplethysmogram sensor assembly includes a first optical sensor operably coupled to the housing within the first groove and a second optical sensor operably coupled to the housing within the second groove. A phonocardiogram sensor is coupled to the second surface of the housing and configured to obtain and push phonocardiogram data to the controller.

According to another aspect, each of a first optical sensor and a second optical sensor is aligned with a window defined by a housing.

According to another aspect, a second surface has a recessed region. A phonocardiogram sensor is coupled to the recessed region of a housing.

According to another aspect, a recessed region defines a recess having at least one of a parabolic shape and a bell shape. A phonocardiogram sensor includes a microphone centrally located within the recess.

According to another aspect, an electrocardiogram sensor assembly includes a first electrode disposed within a first groove and a second electrode disposed within a second groove. The electrocardiogram sensor assembly is configured to obtain electrocardiogram data and send the electrocardiogram data to a controller.

According to another aspect, a second surface of a housing defines a recessed region. An electrocardiogram sensor assembly includes a third electrode coupled to the second surface and extending around the recessed region of the housing.

According to another aspect, a housing is elongated. A first groove and a second groove are positioned along a longitudinal extent of the housing.

According to another aspect, each of a first optical sensor and a second optical sensor includes an emitter and a detector.

According to another aspect of the present disclosure, a medical device includes a housing having a first surface and a second surface. The second surface has a recessed region that defines a recess. A phonocardiogram sensor is coupled to the housing within the recess. The phonocardiogram sensor is configured to obtain phonocardiogram data. An electrocardiogram sensor assembly is coupled to the housing. The electrocardiogram sensor assembly includes a first electrode and a second electrode to obtain electrocardiogram data. A controller is in communication with the phonocardiogram sensor and the electrocardiogram sensor assembly and is configured to process the phonocardiogram data and the electrocardiogram data.

According to another aspect, an electrocardiogram sensor assembly includes a third electrode coupled to a housing and extending around a recess. The electrocardiogram data includes six lead electrocardiogram measurements.

According to another aspect, a first surface of a housing defines a first groove and a second groove. A first electrode is disposed within the first groove and a second electrode is disposed within the second groove.

According to still another aspect, a photoplethysmogram sensor assembly is operably coupled to the housing and configured to obtain and push photoplethysmogram data to a controller.

According to yet another aspect, a photoplethysmogram sensor assembly includes a first optical sensor disposed on a first side of a housing and a second optical sensor disposed on a second side of the housing.

A means for monitoring health including a means for holding having a first surface and a second surface. The first surface defines a first groove on a first side of the means for holding and a second groove on a second side of the means for holding. A means for obtaining photoplethysmogram data includes a first optical sensor disposed in the first groove and a second optical sensor disposed in the second groove. Each of the first optical sensor and the second optical sensor includes an emitter and a detector. A means for obtaining phonocardiogram data is coupled to the second surface of the means for holding. A means for controlling is configured to receive the data from each of the means for obtaining photoplethysmogram data and the means for obtaining phonocardiogram data.

Related applications, for example those listed herein, are fully incorporated by reference. Descriptions within the related applications are intended to contribute to the description of the information disclosed herein as may be relied upon by a person of ordinary skill in the art. Any changes between any of the related applications and the present disclosure are not intended to limit the description of the information disclosed herein, including the claims. Accordingly, the present application includes the description of the information disclosed herein as well as the description of the information in any or all of the related applications.

It will be understood by one having ordinary skill in the art that construction of the described disclosure and other components is not limited to any specific material. Other exemplary embodiments of the disclosure disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the disclosure, as shown in the exemplary embodiments, is illustrative only. Although only a few embodiments of the present innovations have been described in detail in this disclosure, those skilled in the art who review this disclosure will readily appreciate that many modifications are possible (e.g., variations in sizes, dimensions, structures, shapes, and proportions of the various elements, values of parameters, mounting arrangements, use of materials, colors, orientations, etc.) without materially departing from the novel teachings and advantages of the subject matter recited. For example, elements shown as integrally formed may be constructed of multiple parts, or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

What is claimed is:

1. A stethoscope, comprising:

a housing having a first surface and a second surface, wherein the first surface defines a first groove on a first side of the housing and a second groove on a second side of the housing;

a photoplethysmogram sensor assembly operably coupled to the housing and configured to obtain and push photoplethysmogram data to a controller, the photoplethysmogram sensor assembly including:

a first optical sensor operably coupled to the housing within the first groove; and a second optical sensor operably coupled to the housing within the second groove;

a phonocardiogram sensor coupled to the second surface of the housing and configured to obtain and push phonocardiogram data to the controller;

an electrocardiogram sensor assembly coupled to the housing, wherein the electrocardiogram sensor assembly includes a first electrode in the first groove, a second electrode in the second groove, and a third electrode on the second surface; and a power supply operably coupled to the electrocardiogram sensor assembly to provide an electric current, wherein the first electrode is configured to apply the electric current and the second and third electrodes are configured to detect the electric current, and wherein the controller is configured to determine a variance in the electric current detected by the second and third electrodes, and further wherein the controller is configured to determine multiple sub-impedance signals based on the variances and a position of the third electrode relative to a patient body, the position of the third electrode configured to be changed to different locations on the patient body to form multiple vectors in the patient body to calculate the multiple sub-impedance signals for limbs and portions thereof to indicate fluid levels in the limbs and the portions thereof.

2. The stethoscope of claim 1, wherein each of the first optical sensor and the second optical sensor is aligned with a window defined by the housing.

3. The stethoscope of claim 1, wherein the second surface has a recessed region, wherein the phonocardiogram sensor is coupled to the recessed region of the housing.

4. The stethoscope of claim 3, wherein the recessed region defines a recess having at least one of a parabolic shape and a bell shape, and wherein the phonocardiogram sensor includes a microphone centrally located within the recess.

5. The stethoscope of claim 1, wherein the electrocardiogram sensor assembly is configured to obtain electrocardiogram data and send the electrocardiogram data to the controller.

6. The stethoscope of claim 5, wherein the first electrode and the second electrode are contoured to correspond to shapes of the first groove and the second groove, respectively.

7. The stethoscope of claim 1, wherein the second surface of the housing defines a recessed region, and wherein the third electrode extends around the recessed region of the housing.

8. The stethoscope of claim 1, wherein the housing is elongated and flat, and wherein the first groove and the second groove are positioned along a longitudinal extent of the housing, the first groove configured to receive a finger from a first hand and the second groove configured to receive a finger from a second hand.

9. The stethoscope of claim 1, wherein each of the first optical sensor and the second optical sensor includes an emitter and a detector.

10. The stethoscope of claim 9, wherein each emitter is configured to emit infrared light.

11. The stethoscope of claim 1, wherein the electrocardiogram sensor assembly is configured to obtain electrocardiogram data and send the electrocardiogram data to the controller.

12. The stethoscope of claim 11, wherein the controller is configured to determine physiological data from at least one of the photoplethysmogram data, the electrocardiogram data, and the phonocardiogram data, and wherein the physiological data includes at least one of blood pressure, pulse transit time, pulse velocity time, and body composition.

13. The stethoscope of claim 12, wherein the controller is configured to compare the physiological data to predefined values, and wherein the controller is configured to generate an alert notification when the physiological data is outside a predefined range.

14. The stethoscope of claim 11, wherein the electrocardiogram data includes six lead electrocardiogram measurements.

15. The stethoscope of claim 1, wherein the controller is configured to measure an oxygen saturation level in response to the data received from the photoplethysmogram sensor assembly.

16. The stethoscope of claim 1, wherein the controller is configured to determine a pulse transit time and a pulse velocity time of a user in response to the data received from the photoplethysmogram sensor assembly.

17. The stethoscope of claim 1, wherein the second surface defines a centrally located recessed region.

18. The stethoscope of claim 17, wherein the phonocardiogram sensor includes a microphone coupled to the centrally located recessed region of the housing.

19. The stethoscope of claim 18, wherein the microphone is centrally disposed within the centrally located recessed region.

20. The stethoscope of claim 1, further comprising:

buttons on the housing, wherein the buttons correspond with activating a respective one of the photoplethysmogram sensor assembly, the phonocardiogram sensor, and the electrocardiogram sensor assembly.

* * * * *